US007106890B1

(12) United States Patent
Grant et al.

(10) Patent No.: US 7,106,890 B1
(45) Date of Patent: Sep. 12, 2006

(54) ENTERPRISE-WIDE DATA ACCESS TECHNIQUES

(75) Inventors: Robert S. Grant, West Dundee, IL (US); Marc B. Stanis, Wheaton, IL (US); Vinh Truong, Evanston, IL (US); Robert C. Gemperline, Algonquin, IL (US); Mark James Niggemann, Palatine, IL (US); Kumar Ramachandran, Lisle, IL (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/468,155

(22) Filed: Dec. 21, 1999

(51) Int. Cl.
*G06K 9/00* (2006.01)

(52) U.S. Cl. ............... 382/128; 382/132; 711/161; 711/162; 709/217; 709/218; 709/219; 707/204

(58) Field of Classification Search ............... 382/128, 382/131, 132; 709/206, 212, 213, 217–219; 702/183; 600/436, 437, 454; 707/9, 10, 707/204; 711/161, 162
See application file for complete search history.

(56) References Cited

U.S. PATENT DOCUMENTS

| | | | |
|---|---|---|---|
| 5,235,510 A * | 8/1993 | Yamada et al. ............... 600/300 |
| 5,289,548 A * | 2/1994 | Wilson et al. ............... 382/250 |
| 5,642,513 A * | 6/1997 | Schnellinger et al. ....... 717/141 |
| 5,649,185 A * | 7/1997 | Antognini et al. ............. 707/9 |
| 5,812,691 A * | 9/1998 | Udupa et al. ............... 382/128 |
| 5,819,288 A * | 10/1998 | De Bonet ....................... 707/2 |
| 6,115,486 A * | 9/2000 | Cantoni ....................... 382/128 |
| 6,260,021 B1 * | 7/2001 | Wong et al. ................... 705/2 |
| 6,317,743 B1 * | 11/2001 | Heck ........................... 707/10 |
| 6,349,373 B1 * | 2/2002 | Sitka et al. ................. 711/161 |
| 6,389,421 B1 * | 5/2002 | Hawkins et al. ............. 707/10 |
| 6,424,996 B1 * | 7/2002 | Killcommons et al. ..... 709/206 |
| 6,912,317 B1 * | 6/2005 | Barnes et al. ............... 382/239 |

OTHER PUBLICATIONS

Pira, R.S. et al, "Supporting asynchronous telemedicine: Multimedia mail vs. the World Wide Web vs. replicated databases", IEEE Canadian Conference on Electrical and Computer Engineering, May 28, 1999.*
Wu, Cheng-Ta, "Linux means business", Linux Journal, vol. 1999, Issue 57es, Jan. 1999.*
Computer Dictionary, Third edition, Microsoft Press, 1997, ISBN 1-57231-446-X, p. 462.*

(Continued)

*Primary Examiner*—Jingge Wu
*Assistant Examiner*—Shefali Patel
(74) *Attorney, Agent, or Firm*—McAndrews, Held & Malloy, Ltd.; Peter J. Vogel; Michael A. Dellapenna

(57) ABSTRACT

Accessing image data stored in a first storage unit (50) at a first location (1) and a second storage unit (50A) at a second location (1A) is provided by a common server (40) located at location 1. Available imaging data is selected by work stations (60 or 60A) based on the identification data stored in server (40). Selected imaging data is then transferred to a work station from either of the storage units located at the different locations. In case a low speed network is used, transmission of the data from one location to another is facilitated by image transfer servers (80 and 80A).

20 Claims, 2 Drawing Sheets

OTHER PUBLICATIONS

"ImageNet: a global distributed database for color image storage, and retrieval in medical imaging systems", by Martinez et al., Fifth Annual IEEE Symposium on Computer-based Medical Systems, Jun. 17, 1992.*

"An Architecture for Naval Telemedicine", by Chimiak et al., IEEE Transactions on Information Technology in Biomedicien, Vo 1, No. 1, Mar. 1997.*

H.K.Huang, "Picture Archiving and Communication System Components and Industrial Standards," PACS Basic Principles and Applications, A. John Wiley & Sons Publication 1999, Chap 7, pp. 177-198.*

H.K.Huang, "Image Acquisition Gateway," PACS Basic Principles and Applications, A. John Wiley & Sons Publication 1999, Chap 8, pp. 199-231.*

H.K.Huang, "Display Workstation," PACS Basic Principles and Applications, A. John Wiley & Sons Publication 1999, Chap 12, pp. 305-342.* infoRAD, Wu et al., "An Economical, Personal Computer-based Picture Archiving and Communication System," Radiographics, 1999; 19:523-530.*

* cited by examiner

ENTERPRISE-WIDE DATA ACCESS TECHNIQUES

BACKGROUND OF THE INVENTION

This invention relates to picture archiving and communications, and more particularly relates to apparatus and methods which provide access to data stored in multiple image storage units at different locations.

Current picture archiving and communication systems (PACS) operate with individual data bases for images, reference data, and so forth, for each individual site or short-term storage (STS) location. While STS's may be linked, such as in large institutions or hospitals having branches and related organizations, the data bases are nevertheless maintained independently and can only be accessed through a network connection between the STS's. As a result, a user must have knowledge of an image or a data location and perform a query of the system in order to locate a desired image or data. The present invention addresses this problem and provides a solution.

BRIEF SUMMARY OF THE INVENTION

The preferred embodiment is useful in a picture archiving and communication system and includes techniques for locating and accessing image data stored on a first image storage unit at a first location and a second image stored at unit at a second location. The data is created by generating at a first location first imaging data resulting from a first patient and first identification data identifying the first imaging data. First stored image data is stored on the first image storage unit in response to the first imaging data and first stored identification data is stored at the first location in response to the first identification data. The stored identification data preferably is stored on a server located at the first location. Second imaging data resulting from a second patient is generated at the second location, as well as second identification data identifying the second imaging data. Second stored image data is stored on the second image storage unit in response to the second imaging data, and second stored identification data is stored at the first location in response to the second identification data. The second stored identification data preferably is stored on the server located at the first location. The first and second identification data are viewed at the first location by accessing the first and second stored identification data at the first location. At least a first request for transmittal of the second stored image data from the second image storage unit to the first location is made. A second image is created in response to the second stored image data transferred to the first location from the second image storage unit. The first and second identification data also are viewed at the second location by accessing the first and second stored identification data stored at the first location. A second request for transmittal of the first stored image data from the first image storage unit to the second location also is made. A first image is created at the second location in response to the first stored image data transferred to the second location from the first image storage unit.

The creation and viewing of the images preferably is done on work stations located at the first and second locations. The storage of the first and second stored identification data is accomplished preferably by first and second interface units located at the first and second locations.

By using the foregoing techniques, the invention alleviates the need to search various data bases for information relating to images on examinations between linked PACs systems and short-term storage for such systems. The invention simplifies access to the information and offers additional flexibility both in storage and in use of images.

DETAILED DESCRIPTION OF THE INVENTION

Figure 1:
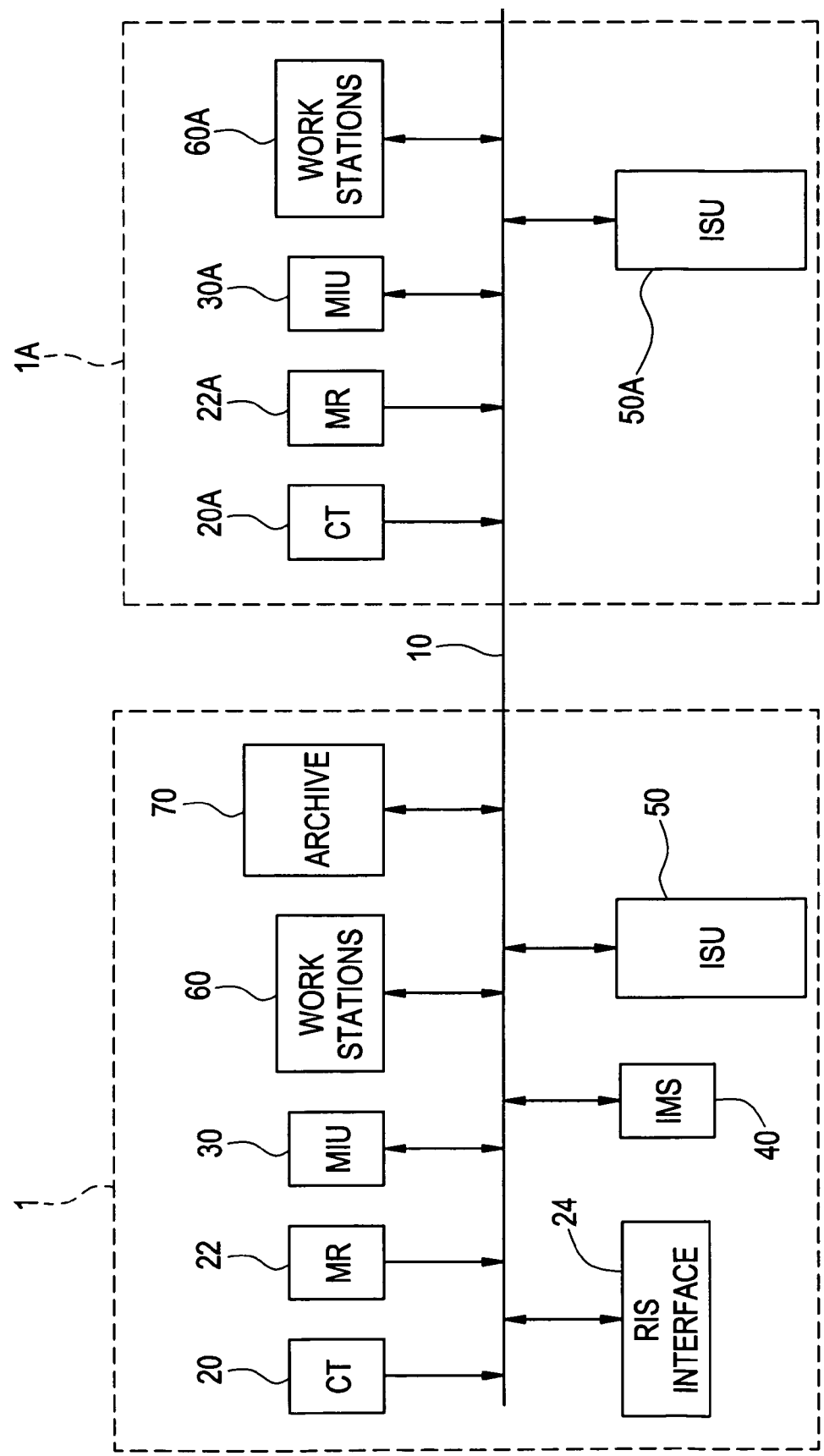
FIG. 1 is a schematic blocked diagram of a preferred form of the invention employing a high speed network for transmitting data between image storage units at different locations.

Referring to FIG. 1, a preferred form of the invention includes a group of components located at a first location 1 such as a hospital, and a group of components located at a second location 1A, such as a clinic which may be several miles from the hospital. The components in locations 1 and 1A are interconnected by a high-speed network 10, such as an ATM network operating at about 155 megabytes per second.

Referring to location 1, a computed tomography unit (CT) 20 images a patient and provides imaging data as well as identification data which is transmitted over network 10 to a modality interface unit 30. The identification data may include the name of the patient, as well as the time and circumstances of the imaging and various identification numbers established by the hospital for identifying the imaging data.

Additional imaging data may be provided by a magnetic resonance imaging device (MR) 22 which also supplies identification data similar to CT 20. The imaging and identification data from MR unit 22 also is transmitted to MIU 30.

MIU 30 sends the identification data through network 10 to an information management server (IMS) 40 which stores the information in any convenient form, including compressed form. MIU 30 compresses the image data and transmits it via network 10 to image storage unit (ISU) 50.

Additional identification data which helps to identify image data also may be provided by a conventional radiology information system (RIS) interface 24. The information from interface 24 also is transmitted over network 10 to IMS 40 for storage and integration with other identification data. One feature of the invention is that a single IMS for identification data is provided for the entire system at both locations 1 and 1A.

Conventional work stations 60 are located at various departments in the hospital in order to view images resulting from the image data and the identification data.

From time to time image data is transmitted from ISU 50 over network 10 to a conventional archive storage unit 70.

At location 1A, components like those described in connection with location 1 also are provided. The corresponding components of location 1A are indicated by the letter A following the identification numeral.

In operation, imaging data resulting from the imaging of a patient, as well as identification data identifying the imaging data, are received from CT 20 and MR 22 through network 10 by MIU 30. MIU 30 transmits the identification data to IMS 40 for storage. MIU 30 also compresses the image data and transmits it to ISU 50.

At location 1A, CT 20A, MR 22A, MIU 30A, and ISU 50A operate in the same manner previously described for the foregoing components at location 1. However, all identification data is stored in IMS 40 located at location 1. The image data from location 1 is stored in ISU 50, whereas the image data created at location 1A is stored in ISU 50A.

In order to view image data stored either on ISU 50 or ISU 50A, a user at the hospital may use any of workstations 60 in order to access the identification data in IMS 40 over network 10. In a well known manner, the identification data is organized by a convenient means, such as alphabetical order or numerical order so that the image data desired for viewing may be quickly identified from the identification data. The user at the work station then causes the work station to transmit a request to ISU 50 and/or ISU 50A for desired image data. The user at one of work stations 60 does not necessarily know the location at which the image data is stored. In response to the request, ISU 50 and/or ISU 50A causes data to transmit to one of work stations 60 for viewing by the user.

After the desired image data is transmitted to one of work stations 60, the work station converts the data into a viewable image which can be interpreted by the user.

Viewing of an image resulting from image data stored in ISU 50 from one of work stations 60A operates in a similar manner. Work stations 60A are able to view the identification data stored in IMS 40 over network 10 until the desired image data is located. One of work stations 60A then generates a signal which requests the desired image data from ISU 50 over network 10 to one of workstations 60A. At one of work stations 60A, the desired image data is converted into an image viewable by the user.

Figure 2:
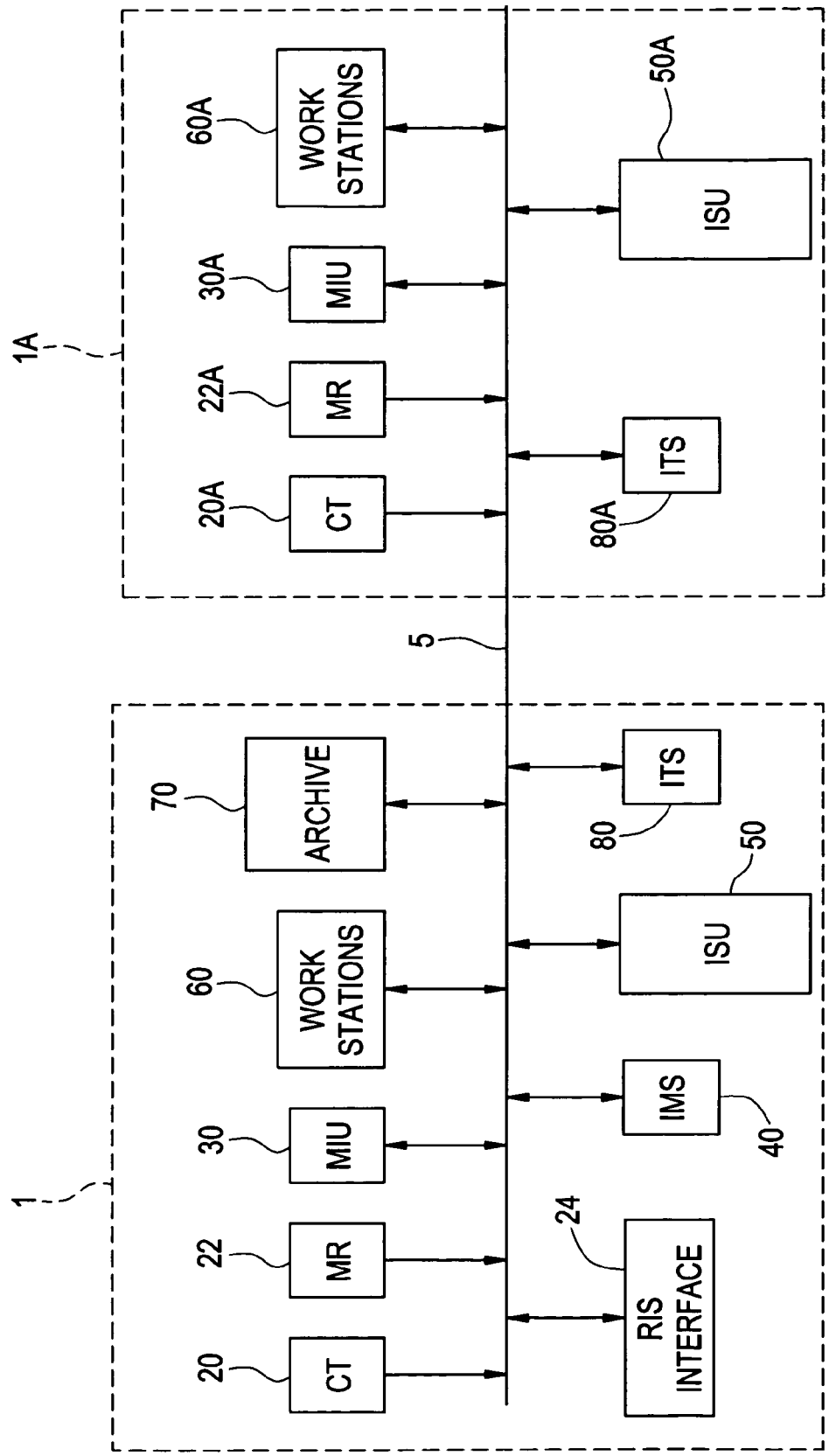
FIG. 2 is a schematic block diagram like FIG. 1 employing a low speed network and incorporating image transfer servers in order to transmit data between information storage units at different locations.

FIG. 2 shows components like those illustrated in FIG. 1 by like numbers. FIG. 2 differs from FIG. 1 in that a low speed network 5 is used in place of high speed network 10. Network 5 may comprise, for example, a T1 telephone line. Because of the slow speed of network 5, image data transfers between locations 1 and 1A are handled by an image transfer server (ITS) 80 at location 1 and a corresponding image transfer server (ITS) 80A at location 1A.

In order for a user at one of work stations 60 to access image data stored on ISU 50A, the user causes the work station to interrogate the identification data in IMS 40 in order to locate the desired image data. The work station then causes a request signal to be sent to IMS 40 which, in turn, requests the desired image data from ISU 50A over network 5. The actual transfer of data takes place from ISU 50A to ISU 50 over network 5 via ITS 80 and ITS 80A in a well known manner. After the information is fetched to ISU 50, the image data is transferred over network 5 to one of work stations 60.

Work stations 60A operate in a similar manner in that they view the identification data in IMS 40 in order to select the desired image data which may be stored in ISU 50. A request is sent from one of work stations 60A to IMS 40, which in turn, causes the desired image data to be transmitted over network 5 by means of ITS 80 and ITS 80A into ISU 50A. Once the desired image data is located in ISU 50A, it may be quickly transmitted to one of work stations 60A for creation of an image for review by the user.

Examples of CT 20, MR 22 and RIS interface 24 are well known to those skilled in the art. An example of MIU 30 is model number 2223612 manufactured by General Electric Company. An example of IMS 40 is model number 2244014 manufactured by General Electric Company. An example of ISU 50 is model number 2223622 manufactured by General Electric Company. Work station 60 and archive 70 are also well known in the art. An example of ITS 80 is model number 2244004 manufactured by General Electric Company.

Those skilled in the art will recognize that the preceding has described the preferred embodiments which may be altered and modified without departing from the true spirit and scope of the invention as defined in the appended claims.

What is claimed is:

1. In a picture archiving and communication system, apparatus for locating and accessing image data stored on a first image storage unit at a first location and a second image storage unit at a second location comprising in combination:

a network extending between the first and second locations;

a single server located at the first location and connected to facilitate transfer of data between the first image storage unit and the second image storage unit through the network;

a first imaging device located at the first location and connected to generate for transmission on the network first imaging data resulting from a first patient and first identification data identifying the first imaging data;

a first interface unit located at the first location and arranged to store first stored image data of the first patient on the first image storage unit in response to the first imaging data and to store first stored identification data on the server located at the first location in response to the first identification data;

a second imaging device located at the second location and connected to generate for transmission on the network second imaging data resulting from a second patient and second identification data identifying the second imaging data;

a second interface unit located at the second location and arranged to store second stored image data of the second patient on the second image storage unit in response to the second imaging data and to store second stored identification data on the server located at the first location in response to the second identification data;

a first workstation located at the first location and connected to create a first image in response to the first stored image data, to create a second image in response to the second stored image data, to view said first and second identification data by accessing said first and second stored identification data in the server through said network and to transmit at least a first request for the second stored image data from the second image storage unit resulting in transfer of the second stored image data from the second image storage unit so that said second image can be created at the first workstation; and a second workstation located at the second location connected to create a third image in response to the first stored image data, to create a fourth image in response to the second stored image data, to view said first and second identification data by accessing said first and second stored identification data in the server through said network and to transmit at least a second request for the first stored image data from the first image storage unit resulting in transfer of the first stored image data from the first image storage unit so that said first image can be created at the second workstation.

2. Apparatus, as claimed in claim 1, wherein said network comprises a high-speed network.

3. Apparatus, as claimed in claim 2, wherein said network comprises an ATM network.

4. Apparatus, as claimed in claim 1, wherein said network comprises a slow-speed network and wherein said apparatus further comprises a first image transfer server located at said first location and a second image transfer server located at the second location, the first and second image transfer servers being connected to transfer the first stored image data to the second image storage unit through the network and to transfer the second stored image data to the first image storage unit through the network.

5. Apparatus, as claimed in claim 4, wherein the network comprises a T-1 telephone line.

6. Apparatus, as claimed in claim 1, and further comprising a radiology information system and wherein a portion of the first identification data is provided by the radiology information system.

7. Apparatus, as claimed in claim 1, wherein the first imaging device comprises a computed tomography unit.

8. Apparatus, as claimed in claim 7, wherein the second imaging device comprises a magnetic resonance imaging device.

9. The apparatus, as claimed in claim 1, wherein the first identification data includes at least one of a first patient's name, time of a first imaging, and circumstances of the first imaging, and wherein the second identification data includes at least one of a second patient's name, time of a second imaging, and circumstances of the second imaging.

10. The apparatus, as claimed in claim 9, wherein the first identification data further includes a first identification number identifying the first stored imaging data, and wherein the second identification data further includes a second identification number identifying the second stored imaging data.

11. In a picture archiving and communication system comprising a first image storage unit at a first location and a second image storage unit at a second location, a method of locating and accessing image data stored on said first and second storage units comprising in combination:

generating at the first location first imaging data resulting from a first patient and first identification data identifying the first imaging data;

storing first stored image data of the first patient on the first image storage unit in response to the first imaging data and storing first stored identification data at the first location in response to the first identification data;

generating at the second location second imaging data resulting from a second patient and second identification data identifying the second imaging data;

storing second stored image data of the second patient on the second image storage unit in response to the second imaging data and storing second stored identification data at the first location in response to the second identification data;

viewing at the first location said first and second identification data by accessing said first and second stored identification data at the first location;

transmitting at least a first request for transmittal of the second stored image data from the second image storage unit to the first location;

creating at the first location a second image in response to the second stored image data transferred to the first location from the second image storage unit;

viewing at the second location said first and second identification data by accessing said first and second stored identification data stored at the first location;

transmitting at least a second request for transmittal of the first stored image data from the first image storage unit to the second location; and creating at the second location a first image in response to the first stored image data transferred to the second location from the first image storage unit.

12. A method, as claimed in claim 11, wherein said transmittals occur on a high-speed network.

13. A method, as claimed in claim 12, wherein said network comprises an ATM network.

14. A method, as claimed in claim 11, wherein said transmittals occur on a slow-speed network.

15. A method, as claimed in claim 14, wherein the network comprises a T-1 telephone line.

16. A method, as claimed in claim 11, and further comprising a radiology information system and wherein a portion of the first identification data is provided by the radiology information system.

17. A method, as claimed in claim 11, wherein said generating at the first location first imaging data comprises computed tomography imaging.

18. A method, as claimed in claim 17, wherein said generating at the second location second imaging data comprises magnetic resonance imaging.

19. The method, as claim in claim 11, wherein the first identification data includes at least one of a first patient's name, time of a first imaging, and circumstances of the first imaging, and wherein the second identification data includes at least one of a second patient's name, time of a second imaging, and circumstances of the second imaging.

20. The method, as claim in claim 19, wherein the first identification data further includes a first identification number identifying the first stored image data, and wherein the second identification data further includes a second identification number identifying the second stored image data.

* * * * *